(12) United States Patent
Harrelson et al.

(10) Patent No.: US 11,266,610 B2
(45) Date of Patent: Mar. 8, 2022

(54) CINNAMALDEHYDE DERIVATIVE COMPOUNDS, AND METHODS OF USE FOR CINNAMALDEHYDE DERIVATIVE COMPOUNDS NICOTINE CESSATION

(71) Applicant: PACIFIC UNIVERSITY, Forest Grove, OR (US)

(72) Inventors: John P. Harrelson, Forest Grove, OR (US); Deepa A. Rao, Beaverton, OR (US)

(73) Assignee: PACIFIC UNIVERSITY, Forest Grove, OR (US)

( * ) Notice: Subject to any disclaimer, the term of this patent is extended or adjusted under 35 U.S.C. 154(b) by 0 days.

(21) Appl. No.: 16/663,291

(22) Filed: Oct. 24, 2019

(65) Prior Publication Data

US 2020/0129449 A1    Apr. 30, 2020

Related U.S. Application Data

(60) Provisional application No. 62/750,147, filed on Oct. 24, 2018.

(51) Int. Cl.
| | |
|---|---|
| A61K 31/11 | (2006.01) |
| A61P 25/34 | (2006.01) |
| A61K 9/00 | (2006.01) |
| A61K 31/465 | (2006.01) |

(52) U.S. Cl.
CPC ............ *A61K 31/11* (2013.01); *A61K 9/0053* (2013.01); *A61K 31/465* (2013.01); *A61P 25/34* (2018.01)

(58) Field of Classification Search
CPC ..... A61K 31/11; A61K 31/465; A61K 9/0053
See application file for complete search history.

(56) References Cited

PUBLICATIONS

Ilangovan et al. (Journal of the Korean Chemical Society, 2011, vol. 55, No. 6; p. 1000-1006).*
Elvira, G., "Patent protection for a new use of a known compound.," Smart & Bigger Website, Available Online at https://www.smartbiggar.ca/insights/publication/patent-protection-for-a-new-use-of-a-known-compound, Sep. 20, 2012, 5 pages.

(Continued)

*Primary Examiner* — Valerie Rodriguez-Garcia
(74) *Attorney, Agent, or Firm* — McCoy Russell LLP

(57) ABSTRACT

Compounds, compositions, and methods of use of such compounds and compositions are provided for reducing human dependency to nicotine. In one example, a method of treating an individual with an addiction to nicotine comprises administering to the individual a compound that is a structural analog of trans-cinnamaldehyde ((2E)-3-Phenyl-prop-2-enal):

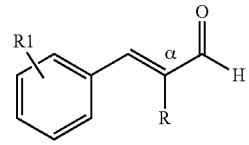

Based on the administration, a rate at which nicotine is metabolized may be reduced, which in turn may reduce a desire for the individual to consume nicotine-containing products.

3 Claims, 13 Drawing Sheets

(56) References Cited

PUBLICATIONS

Chenoweth, M. et al., "CYP2A6 slow nicotine metabolism is associated with increased quitting by adolescent smokers," Pharmacogenetics and Genomics, vol. 23, No. 4, Apr. 2013, 7 pages.

Chan, J. et al., "Inactivation of CYP2A6 by the Dietary Phenylpropanoid trans-Cinnamic Aldehyde (Cinnamaldehyde) and Estimation of Interactions with Nicotine and Letrozole," Drug Metabolism and Disposition: the biological fate of chemicals, vol. 44, No. 4, Apr. 2016, Available Online Feb. 5, 2016, 10 pages.

Sivinski, S., "Vanda v. West-Ward: This Time, Dosage Adjustment Claims are Patent Eligible Subject Matter," IP Watchdog Website, Available Online at https://www.ipwatchdog.com/2018/05/16/vanda-v-west-ward-dosage-adjustment-claims-patent-eligible/id=97117/, May 16, 2018, 15 pages.

Soeroso, N. et al., "Genetic Polymorphism of CYP2A6 and Its Relationship with Nicotine Metabolism in Male Bataknese Smokers Suffered from Lung Cancer in Indonesia," Open Access Macedonian Journal of Medical Sciences, vol. 6, No. 7, Jul. 15, 2018, 7 pages.

True, H. et al., "Structure-Toxicity Relationships of Trans-Cinnamic Aldehyde and Its Substituted Analogs," The FASEB Journal Website, Available Online at https://www.fasebj.org/doi/abs/10.1096/fasebj.2019.33.1_supplement.672.6, Apr. 1, 2019, 3 pages.

\* cited by examiner

FIG. 5B
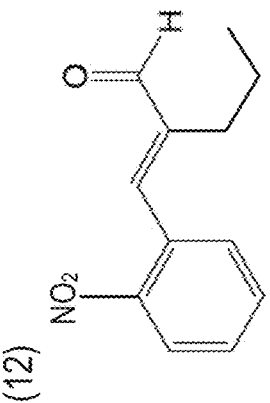
(11)
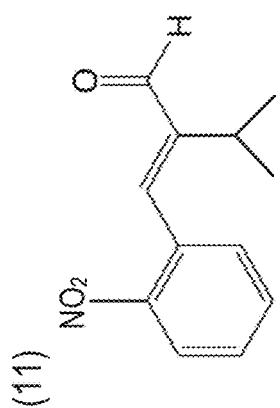
(10)
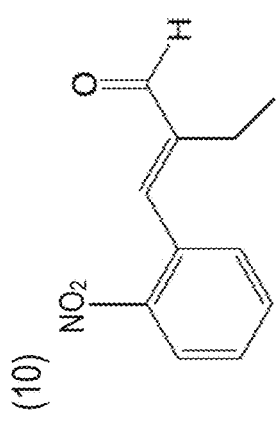
(13)
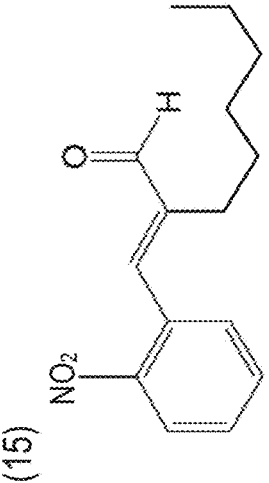
(12)
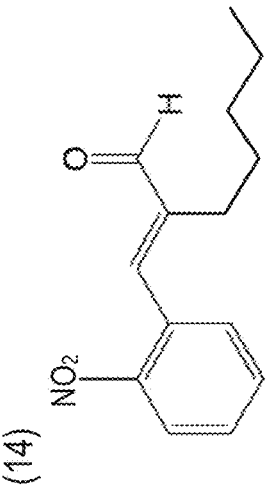
(14)
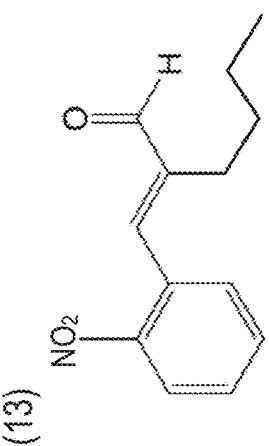
(15)

FIG. 6

| Analog | ADV Rigid Kd (µM) | STDEV (µM) | Minimum | Maximum | Range (µM) |
|---|---|---|---|---|---|
| Trans-cinnamaldehyde | 16.8 | 1.6 | 5.2 | 152.8 | 147.6 |
| 4-(Dimethylamino)cinnamaldehyde | 44.7 | 3.5 | 23.8 | 214.2 | 190.4 |
| Trans-4-(Diethylamino)cinnamaldehyde | 23.4 | 2.0 | 10.2 | 180.9 | 170.7 |
| (e)-3-benzo[1,3]dioxol-5-yl-2-methyl-propenal | 6.3 | 0.7 | 1.1 | 77.7 | 76.6 |
| 2-Methoxycinnamaldehyde, trans | 28.2 | 2.8 | 3.7 | 152.8 | 149.1 |
| 3-(4-Tert-Butyl-Phenyl)-2-Methyl-Propenal | 38.4 | 0.5 | 33.4 | 46.8 | 13.4 |
| alpha-Methyl-trans-cinnamaldehyde | 3.2 | 0.2 | 1.9 | 77.7 | 75.8 |
| alpha-Hexylcinnamaldehyde | 16.7 | 1.4 | 3.7 | 77.7 | 74.0 |
| alpha-Amylcinnamaldehyde | 8.5 | 0.8 | 1.6 | 77.7 | 76.1 |
| Alpha-Bromocinnamaldehyde | 6.0 | 0.5 | 2.6 | 92.0 | 89.4 |
| Alpha-Chlorocinnamaldehyde | 5.7 | 0.4 | 3.1 | 129.1 | 125.9 |
| 4-Bromocinnamaldehyde | 16.8 | 1.1 | 10.2 | 129.1 | 118.8 |
| 4-Fluorocinnamaldehyde | 9.2 | 0.8 | 3.7 | 180.9 | 177.2 |
| 4-Chlorocinnamaldehyde | 15.5 | 1.5 | 6.2 | 214.2 | 208.1 |
| 2,6-DiFluorocinnamaldehyde | 4.0 | 0.2 | 1.6 | 55.4 | 53.8 |
| 2-Nitrocinnamaldehyde | 17.1 | 1.6 | 3.7 | 92.0 | 88.3 |
| 4-Nitrocinnamaldehyde | 12.9 | 0.8 | 3.7 | 92.0 | 88.3 |
| 3-Nitrocinnamaldehyde | 13.2 | 0.7 | 7.3 | 92.0 | 84.7 |
| Cinnamonitrile | 9.3 | 0.8 | 3.7 | 129.1 | 125.3 |
| Cinnamaldehyde Oxime | 14.8 | 1.0 | 7.3 | 129.1 | 121.8 |
| 3-Phenylpropionaldehyde | 13.5 | 0.7 | 6.2 | 180.9 | 174.8 |
| Beta-Phenylcinnamaldehyde | 1.6 | 0.2 | 0.6 | 17.0 | 16.4 |
| 3-(3-Pyridyl)acrolein | 41.8 | 3.2 | 17.0 | 421.1 | 404.2 |

CINNAMALDEHYDE DERIVATIVE COMPOUNDS, AND METHODS OF USE FOR CINNAMALDEHYDE DERIVATIVE COMPOUNDS NICOTINE CESSATION

CROSS REFERENCE TO RELATED APPLICATIONS

The present application claims priority to U.S. Provisional Application No. 62/750,147, entitled "AGENTS FOR NICOTINE CESSATION AND CHEMOPREVENTION," and filed on Oct. 24, 2018. The entire contents of the above-referenced application are hereby incorporated by reference for all purposes.

ACKNOWLEDGMENT OF GOVERNMENT SUPPORT

This invention was made with government support under Grant Number: 1R15DA042341-01 awarded by the National Institute on Drug Abuse. The government has certain rights in this invention.

FIELD OF THE INVENTION

The present invention pertains to compounds, compositions, and methods of use for chemical compounds found to inhibit the primary human nicotine metabolizing enzyme, cytochrome P450 2A6 (CYP2A6). The compositions and methods of use may reduce a frequency at which products containing nicotine are consumed, and may reduce an exposure of individuals to carcinogenic substances over time.

BACKGROUND OF THE INVENTION

Nicotine is the addictive agent in cigarettes. Tobacco users alter their smoking behavior/smoke exposure to maintain nicotine plasma concentrations within a defined range (e.g., 10 to 50 ng/mL). Nicotine elimination occurs mainly through metabolism, and factors reducing nicotine metabolism may result in fewer cigarettes smoked per day due to nicotine concentrations being maintained for longer periods. Conversely, rapid nicotine metabolism may result in elevated smoking rates and carcinogen exposure, as smokers must increase nicotine exposure to maintain plasma concentrations. Although nicotine addiction is a complex disease involving many factors, nicotine plasma concentration is a central factor.

Tobacco addiction is the leading global cause of preventable death. Aside from contributing to preventable death, tobacco addiction poses other substantial problems, such as diverting funds from other important health problems, and disproportionately impacting lower income families/individuals. Considering the adverse impact of tobacco addiction on health, the current number of treatments for decreasing tobacco use is severely deficient. Unlike many disease states for which there are many treatment options to account for variability in patient response, currently there are only three pharmacological approaches approved by the U.S. Food and Drug Administration to treat nicotine addiction. These include nicotine replacement therapy, bupropion, and varenicline. Alternative approaches (e.g. meditation, hypnosis, and others) have been used but the effectiveness of these approaches is vague or has not been studied extensively. By contrast, there are 29 drugs for depression and 33 for diabetes, for example. Thus, there is a need for compounds that can reduce the urge to smoke (or consume other nicotine-containing products), thereby reducing a potential for adverse health implications.

Cytochrome P450 2A6 (CYP2A6) is an enzyme responsible for metabolizing 70-80% of a nicotine dose. CYP2A6 displays wide genetic variability with more than 37 known polymorphisms to date. Some of these polymorphisms result in a CYP2A6 enzyme with reduced nicotine metabolizing activity. Genetic-based differences in nicotine metabolism influence smoking behavior and cigarette smoke exposure. Indeed, individuals with CYP2A6 variants that are poor metabolizers of nicotine smoke fewer cigarettes and have higher smoking cessation success rates than individuals expressing a variant of the CYP2A6 enzyme that extensively metabolizes nicotine.

It has been previously shown that trans-cinnamaldehyde (t-CA), also referred to herein as CA), comprising a low-molecular weight phenylpropanoid present in cinnamon (which contributes to cinnamon's flavor and aroma and is a major component of cinnamon oil), is a mechanism-based irreversible inhibitor (MBI) of CYP2A6. MBIs are also often referred to as time-dependent inhibitors (TDI), particularly in the drug-drug interaction literature associated with the pharmaceutical industry and related guidance from the United States Food and Drug Administration.

It is herein recognized that genetic variability (>37 polymorphisms to date, as discussed above) with regard to CYP2A6 may result in t-CA being effective in inhibiting CYP2A6 in some cases (thereby slowing a rate at which nicotine is metabolized), while not being as effective in other cases. Thus, it is herein recognized that there may be particular structural analogs of t-CA which may be more effective in certain cases, as compared to others. Furthermore, it is herein recognized that there may be structural analogs of t-CA which are more potent than t-CA, and which may thus be more effective at reducing an urge to consume nicotine-containing products.

Another cytochrome p450 enzyme CYP2A13, is localized in the lung, and shows overlapping substrate specificity with CYP2A6. Specifically, it has been previously shown that CYP2A13 can catalyze the metabolism of nicotine. CYP2A13 also catalyzes the metabolism of tobacco-specific nitrosamines, which contributes to carcinogenic processes and lung cancer. Accordingly, it is herein recognized that particular structural analogs of t-CA may in some examples inhibit CYP2A13, which may reduce a rate at which nicotine is metabolized and also reduce the activation of tobacco-specific carcinogens to metabolites that alkylate DNA.

SUMMARY

The present disclosure provides compounds, compositions, and methods of use for such compounds and compositions that may possess improved ability to inhibit/inactivate CYP2A6. The improved ability may relate to an increased inhibition potency as compared to t-CA, for example. The improved ability may relate to a particular t-CA structural analog displaying increased potency for a particular CYP2A6 genotype, in other examples. Similarly, the improved ability may relate to a particular t-CA structural analog being more effective than other t-CA structural analogs (or t-CA itself) with regard to how nicotine is metabolized in a particular individual (e.g., whether the particular individual is an ultrafast, fast, intermediate, or slow metabolizer of nicotine). In some examples, the compounds, compositions and methods of use for such compounds and compositions may additionally or alternatively possess an ability to inhibit/inactivate CYP2A13.

The compounds of the present disclosure may include α-bromocinnamaldehyde, α-chlorocinnamaldehyde, 2-nitrocinnamaldehyde, 2-trifluoromethylcinnamaldehyde, 2,6-difluorocinnamaldehyde, 2-methoxycinnamaldehyde, 3-nitrocinnamaldehyde, 4-nitrocinnamaldehyde and 2-nitro-α-methylcinnamaldehyde, 2-nitro-α-ethylcinnamaldehyde, 2-nitro-α-propylcinnamaldehyde, 2-nitro-α-isopropylcinnamaldehyde, 2-nitro-α-butylcinnamaldehyde, 2-nitro-α-amylcinnamaldehyde, 2-nitro-α-hexylcinnamaldehyde, and hydrocinnamaldehyde. The above-mentioned compounds may be time-dependent inhibitors of CYP2A6 and/or CYP2A13. In some examples, a method for treating an individual with an addiction to nicotine may comprise administering to the individual one or more of the above-mentioned chemical structures, wherein a rate at which nicotine is metabolized is reduced upon administration of the compound to the individual. In such a method, a genetic variant of CYP2A6 may in some examples be determined, wherein selection of the compound to administer may be based on the genetic variant. In some examples, selection of the compound to administer may be based on whether the individual is an ultrafast, fast, intermediate, or slow metabolizer of nicotine. The one or more compounds may be administered orally to the individual.

Another embodiment of the present disclosure may include a pharmaceutical composition for reducing a rate at which nicotine is metabolized, where the pharmaceutical composition comprises one or more of the above-mentioned compounds (α-bromocinnamaldehyde, α-chlorocinnamaldehyde, 2-nitrocinnamaldehyde, 2-trifluoromethylcinnamaldehyde, 2,6-difluorocinnamaldehyde, 2-methoxycinnamaldehyde, 3-nitrocinnamaldehyde, 4-nitrocinnamaldehyde and 2-nitro-α-methylcinnamaldehyde, 2-nitro-α-ethylcinnamaldehyde, 2-nitro-α-propylcinnamaldehyde, 2-nitro-α-isopropylcinnamaldehyde, 2-nitro-α-butylcinnamaldehyde, 2-nitro-α-amylcinnamaldehyde, 2-nitro-α-hexylcinnamaldehyde, 2-methoxycinnamaldehyde, and hydrocinnamaldehyde). For such a composition, the rate at which nicotine is metabolized may be reduced based on the pharmaceutical composition inhibiting an enzyme (e.g., CYP2A6, CYP2A13) that metabolizes nicotine. The composition may in some examples further comprise an oil. Additionally or alternatively, the composition may further comprise a surfactant. Additionally or alternatively, the composition may further comprise a co-surfactant.

Another embodiment of the present disclosure includes structural analogs of t-CA (such as the compounds discussed above), additionally designed to specifically protect t-CA (or structural analogs thereof) from being degraded. Specifically, while t-CA is well-absorbed in the intestinal tract following oral administration, clearance is rapid, as the aldehyde group of t-CA (and structural analogs thereof) may be susceptible to metabolism by a variety of pathways. Thus, in one aspect of the present invention, the rate of t-CA (or structural analogs thereof) degradation may be reduced by utilizing a 'prodrug' oxime-ether form of t-CA (or structural analogs thereof), which may protect the aldehyde group from degrading as the t-CA (or structural analogs thereof) travels to its therapeutic target.

In another aspect of the disclosure, the rate of degradation of t-CA (or structural analogs thereof) may be reduced by, as a first example, utilizing a first formulation that includes a co-solvent solution using tri-block co-polymers. t-CA (and structural analogs thereof) may be incorporated into such tri-block co-polymers by a solvation method. In one example, the tri-block co-polymers (e.g., polaxamers) are selected based on an enhancement in the oral bioavailability of t-CA (and structural analogs thereof). However, other tri-block co-polymers may be used without departing from the scope of this disclosure. In some examples, block co-polymers comprising PEG-PCL or PEG-PLA, may be used to obtain higher drug concentrations.

In another aspect of the disclosure, a self-emulsifying drug delivery system (SEDDS) may be utilized to formulate a second formulation that includes t-CA or structural analogs thereof. Briefly, a SEDDS may comprise physically stable mixtures of oil, surfactants, co-surfactants and solubilized drug substances (e.g. t-CA and structural analogs thereof), which may then be administered orally (in soft or hard gelatin capsules for example). The oil may be a long chain triglyceride, a medium chain triglyceride, etc., with varying degrees of saturation. The surfactants may be anionic surfactants, cationic surfactants, ampholytic surfactants, nonionic surfactants, etc. Examples of anionic surfactants of the present disclosure include potassium laurate and sodium lauryl sulphate. An example of a cationic surfactant of the present disclosure includes quaternary ammonium halide. An example of ampholytic surfactants of the present disclosure include sulfobetaines. An example of nonionic surfactants of the present disclosure include sorbitan esters (Spans) and polysorbates (Tweens). In a gastrointestinal tract environment, the SEDDS may spontaneously emulsify. In developing the SEDDS, particular surfactant/particular mixtures of surfactants may be selected to match a Hydrophile-Lipophile Balance (HLB) value for t-CA oil (or structural analogs thereof). t-CA (and structural analogs thereof) loading and stability may be assessed by monitoring size and zeta potential. t-CA (and structural analogs thereof) release may be assessed by a dialysis method under sink conditions.

In this way, an individual's dependence on nicotine may be reduced. In some examples, by relying on the compounds, compositions, formulations and methods discussed herein, an individual may be able to completely quit their use of nicotine-containing products. Dosages and selection of particular compounds may in some examples be based on how an individual metabolizes nicotine. For example, a first compound may be administered to an individual who is determined to be a fast metabolizer of nicotine, whereas a second compound may be administered to an individual who is determined to be a slow metabolizer of nicotine. For example, the first compound may have a greater potency with regard to CYP2A6 inhibition, as compared to the second compound. In other examples, a same compound may be administered to both an individual that is a fast metabolizer of nicotine and an individual that is a slow metabolizer of nicotine, but a dosage may be greater for the individual that is the fast metabolizer, as compared to the individual that is the slow metabolizer. Determining whether an individual is a fast or slow (or in other examples also ultrafast and intermediate) metabolizer of nicotine may be accomplished by methodology readily available to those of ordinary skill in the art. As examples, nicotine metabolism in an individual may be measured (e.g., by monitoring nicotine metabolites as will be elaborated in further detail below), may be determined based on a genetic profile of CYP2A6 (or in some examples CYP2A13) for the individual, or may be qualitatively determined based on an interview or questionnaire provided to the individual who desires to reduce their dependence on nicotine.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

FIGS. 5A-5B depict a select number of structural analogs of t-CA prepared via substitutions as depicted at FIGS. 4A-4C;

FIG. 6 depicts an example dataset of dissociation constants for structural analogs of CA as determined via a molecular docking approach;

DETAILED DESCRIPTION OF THE INVENTION

The compounds, formulations, compositions and/or methods of use of such compounds and/or formulations discussed herein may improve an ability for individuals with an addiction to nicotine to reduce their consumption of nicotine-containing products, which may thus result in such individuals reducing a potential risk for adverse health implication that result from their consumption of nicotine-containing products.

Figure 1:
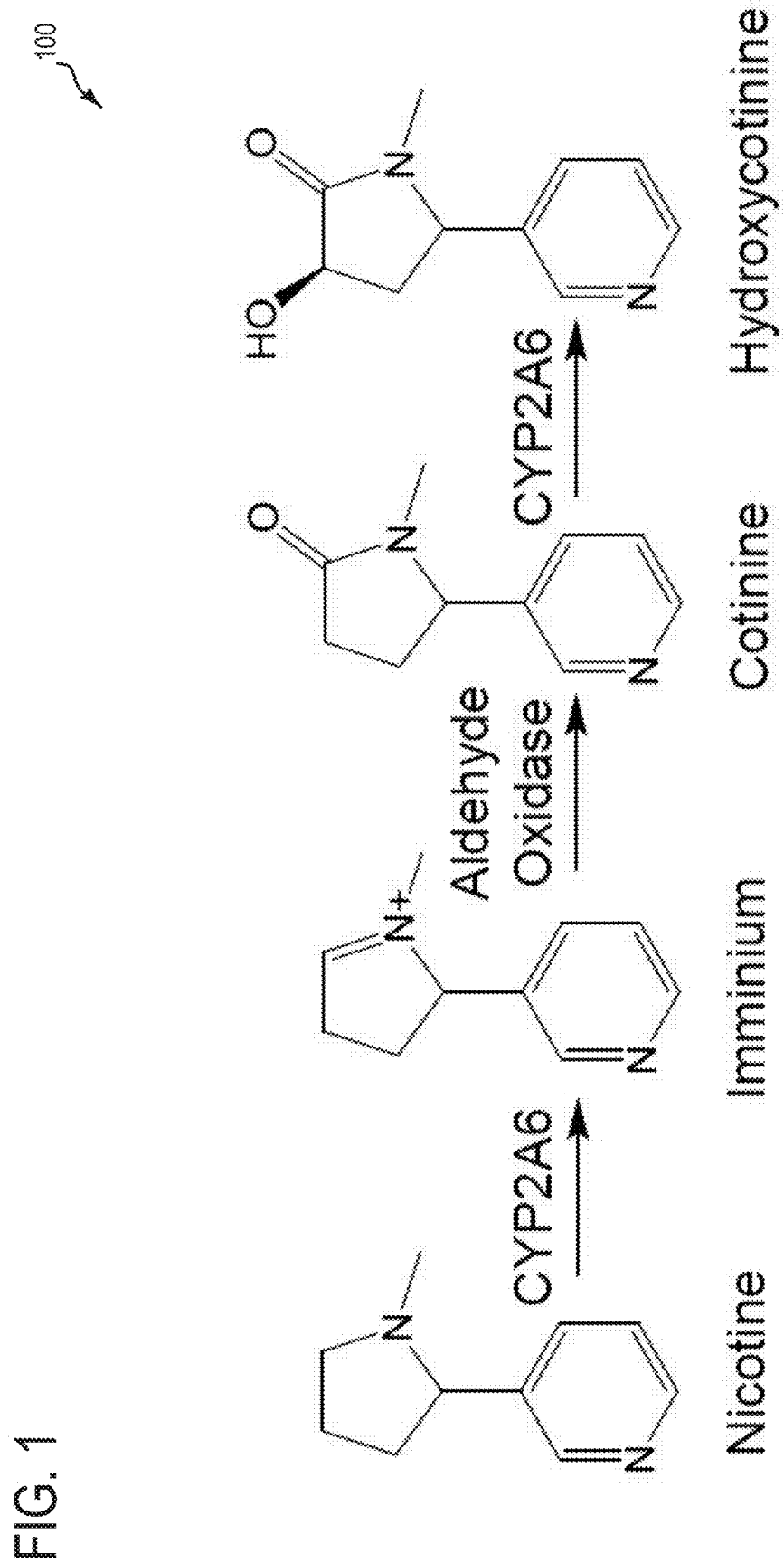
FIG. 1 depicts a scheme whereby nicotine is metabolized to cotinine by CYP2A6.

Turning to FIG. 1, example scheme 100 illustrates that CYP2A6 metabolizes nicotine to an iminium ion, which is further metabolized via aldehyde oxidase to cotinine, the major blood-circulating metabolite of nicotine. As depicted, cotinine may be further metabolized by CYP2A6 to hydroxycotinine. As mentioned above, a rate at which nicotine is metabolized via the example scheme 100 may be different for different individuals based on their particular CYP2A6 genetic subtype. As is known in the art, it may be possible to determine rates of metabolism of nicotine for different individuals by evaluating a hydroxycotinine/cotinine ratio as a function of time in blood samples of different individuals after consumption of nicotine-containing products. In another example, as is known in the art, it may be possible to infer rates of metabolism (e.g., ultrafast, fast, intermediate, slow) based on determined CYP2A6 genotype. Briefly, DNA or mRNA from a biological sample of an individual may be obtained, and the CYP2A6 subtype may be determined by amplifying the CYP2A6 region to prepare a DNA sample enriched in DNA from the CYP2A6 gene region, and then sequencing the DNA sample to determine if the individual is an ultrafast, fast, intermediate, or slow metabolizer of nicotine. In other examples, such methodology may simply characterize an individual as a fast metabolizer or a slow metabolizer. By determining rates of metabolism of nicotine in different individuals, it may be possible to select a particular structural analog of t-CA (see FIGS. 4A-5B) that are more effective for a particular individual. In other words, a particular t-CA structural analog may be more effective than another t-CA structural analog for an individual determined to be a fast metabolizer of nicotine, for example.

Figure 2:
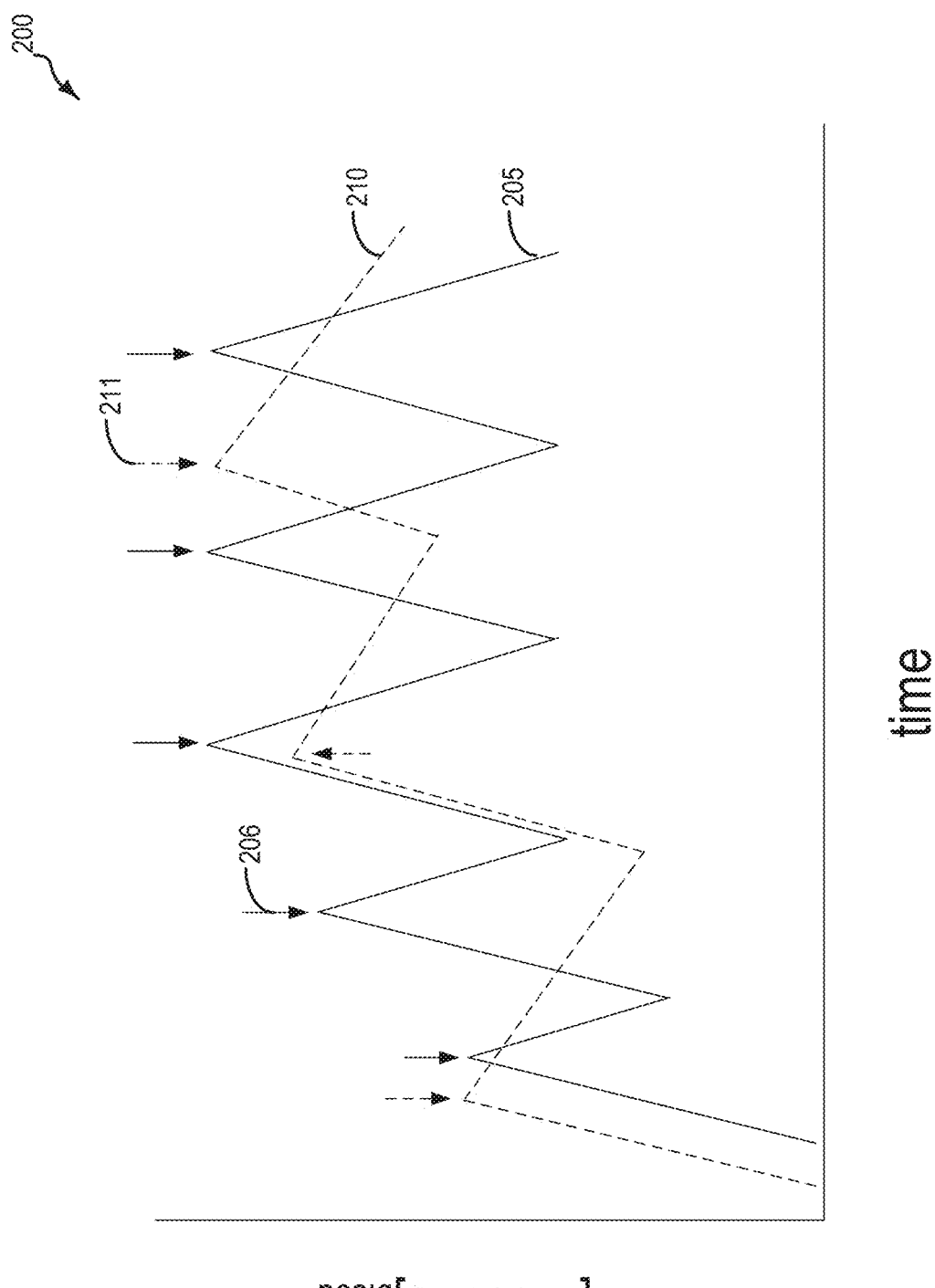
FIG. 2 depicts an example illustration of different metabolism rates of nicotine for individuals that are slow metabolizers of nicotine as compared fast metabolizers of nicotine.

For illustrative purposes, FIG. 2 depicts example illustration 200, illustrating a relationship between nicotine concentration in blood (y-axis), over time (x-axis), for an individual with a CYP2A6 variant that rapidly metabolizes nicotine (line 205), compared to an individual that slowly metabolizes nicotine (line 210). Solid arrows 206 correspond to peaks of line 205, and represent times when a cigarette is smoked for the individual that rapidly metabolizes nicotine. Similarly, dashed arrows 211 correspond to peaks of line 210, and represent times when a cigarette is smoked for the individual that slowly metabolizes nicotine. As can be seen, the individual that metabolizes nicotine slower smokes less over time (three cigarettes as compared to five). The compounds (e.g., structural analogs of t-CA) discussed herein may, for example, modify an individual's nicotine metabolism such that when the compound is administered, the individual has a reduced desire to consume nicotine-containing products.

Specifically, based on the relationship between nicotine metabolism and smoking behavior, as smokers typically 'wean' off nicotine and continue to smoke while they attempt to quit, CYP2A6 inhibitors may help smokers maintain blood nicotine concentrations for longer periods, such that a time between smoking episodes may be extended, which may thus improve efforts to resist the routines (e.g., "smoke breaks") that contribute to smoking addiction and potential adverse health consequences stemming therefrom.

Figure 3A:
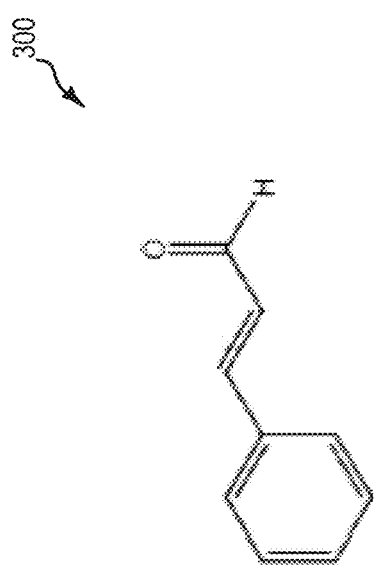
FIG. 3A depicts a structural representation of trans-cinnamaldehyde (t-CA)
Figure 3B:
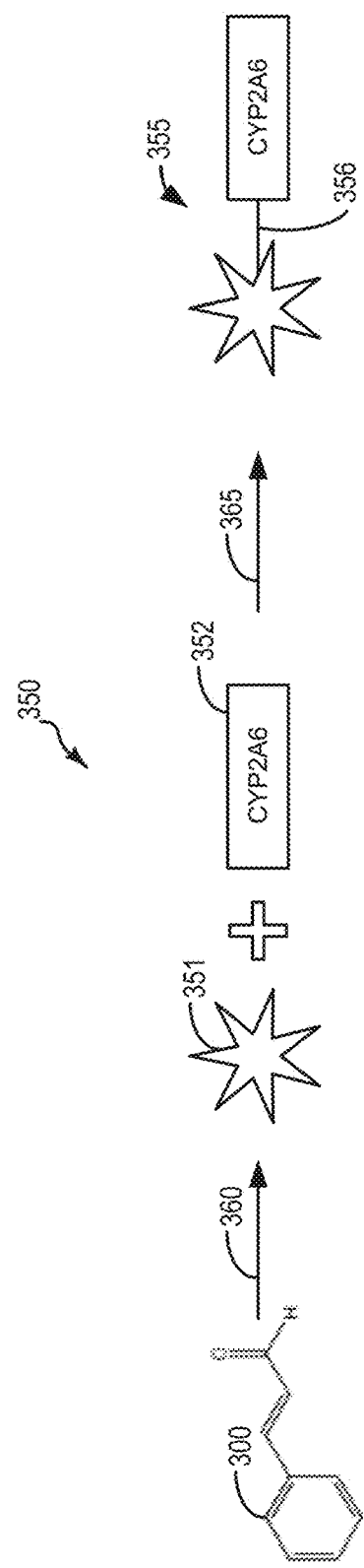
FIG. 3B depicts a reaction scheme whereby t-CA inhibits CYP2A6.

Turning to FIG. 3A, depicted is a chemical structure 300 of t-CA. As mentioned above, t-CA is an MBI (also referred to as a TDI) of CYP2A6. Accordingly, FIG. 3B depicts an illustrative scheme 350 for the mechanism-based inhibition of CYP2A6. Specifically, t-CA 300 undergoes metabolism by CYP2A6 (depicted as arrow 360), such that t-CA 300 is metabolized to a CA reactive metabolite 351. In the presence of CYP2A6 352, a step 365 in which the CA reactive metabolite 351 binds (depicted as line 356) CYP2A6 352 results in an inactivated CYP2A6 355. Because MBIs such as t-CA irreversibly inactivate the enzyme to which they bind, MBIs may offer an advantage in that they may provide a prolonged inhibition (prolonged nicotine inhibition in the case of CYP2A6 inhibition), as compared to reversible inhibitors. In other words, because the particular enzyme (e.g. CYP2A6) becomes permanently inactivated, in order to reinstate the metabolizing activity of the particular enzyme, the particular enzyme may first have to be regenerated, which may be dependent on the intrinsic rate of expression of the particular enzyme in a particular cell type (e.g. intrinsic rate of expression of CYP2A6 in hepatocytes).

FIGS. 3A-3B depict t-CA for illustrative purposes. As discussed above, it is herein recognized that t-CA may effectively inhibit CYP2A6 for some individuals, but may be less effective or ineffective in other examples depending on the individual's CYP2A6 genotype. It is further herein recognized that structural analogs of t-CA may provide greater potential for CYP2A6 inhibition than t-CA, which may further be a function of CYP2A6 genotype (or in other words, based on how nicotine is metabolized in particular individuals). Thus, there may be particular advantages to the use of structural analogs of t-CA in terms of reducing consumption of nicotine-containing products and thereby reducing particular individual's exposure to carcinogenic substances.

Figure 4A:
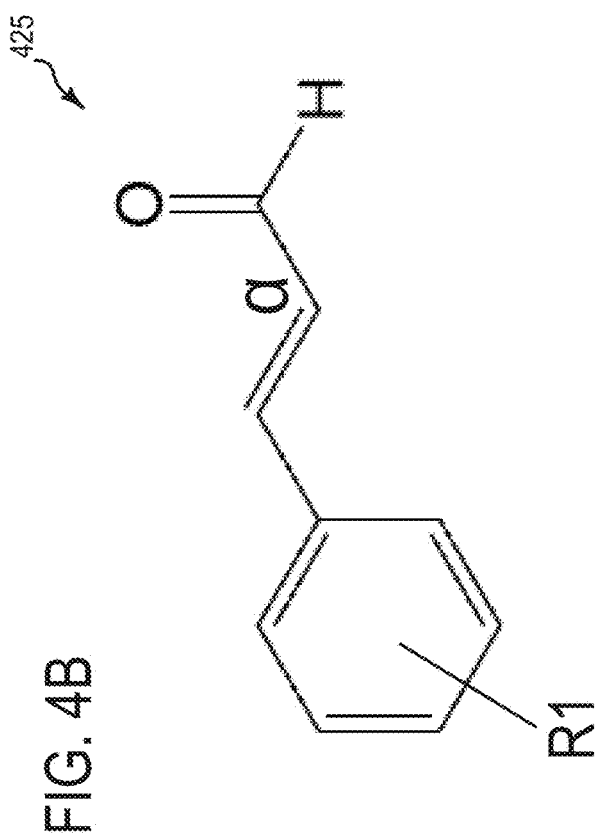
FIGS. 4A-4C depict options for chemical substitutions to t-CA.
Figure 5A:
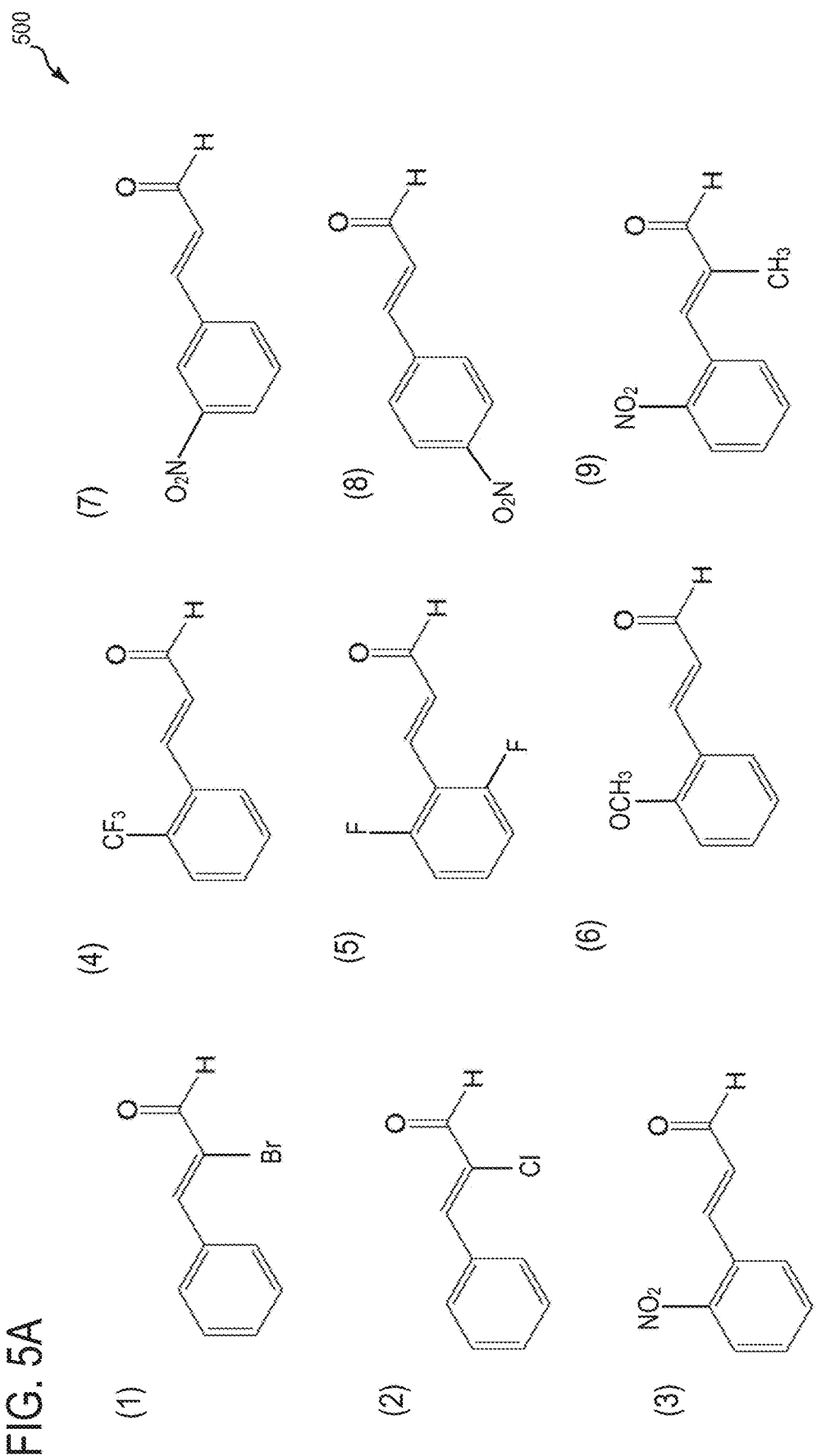

The structural analogs of t-CA relevant to the present disclosure are now discussed. As one example, FIG. 4A shows example illustration 400, depicting t-CA substituted at the alpha position. Structural analogs of the present disclosure as depicted at FIG. 4A may include a halogen substituted at the alpha position of t-CA, for example. Specifically, FIG. 5A depicts a set of compounds 500 relevant to the present disclosure. Compounds (1) and (2) at FIG. 5A illustrate structural analogs substituted with a halogen at the alpha position of t-CA. Specifically, compound (1) is α-bromocinnamaldehyde, and compound (2) is α-chlorocinnamaldehyde.

Figure 4B:
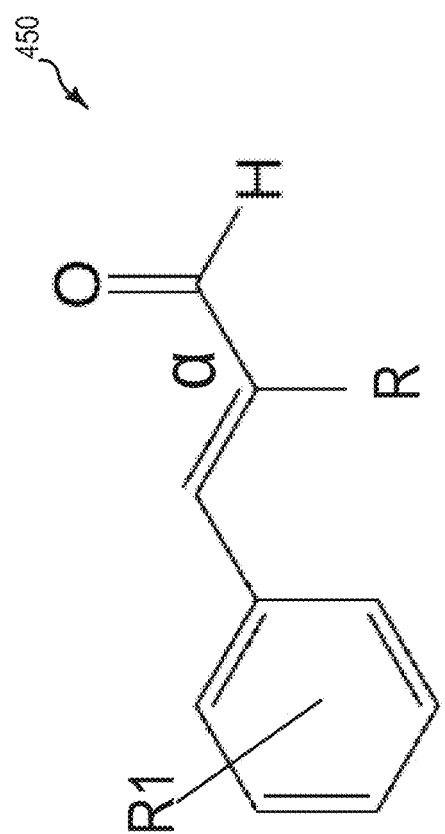

FIG. 4B shows example illustration 425, depicting t-CA substituted at the ring position. Structural analogs of the present disclosure as depicted at FIG. 4B may include substitution at one or more of the ortho, meta, and para positions of the ring. Examples of such compounds relevant to the present disclosure are depicted at FIG. 5A. Specifically, ortho-substituted analogs of t-CA relevant to the present disclosure are depicted by compounds (3), (4), (5), and (6). Compound (3) is 2-nitrocinnamaldehyde, compound (4) is 2-trifluoromethylcinnamaldehyde, compound (5) is 2,6-difluorocinnamaldehyde, and compound (6) is 2-methoxycinnamaldehyde. A meta-substituted analog of t-CA relevant to the present disclosure is depicted by compound (7). Compound (7) is 3-nitrocinnamaldehyde. A para-substituted analog of t-CA relevant to the present disclosure is depicted by compound (8). Compound (8) is 4-nitrocinnamaldehyde.

Figure 4C:
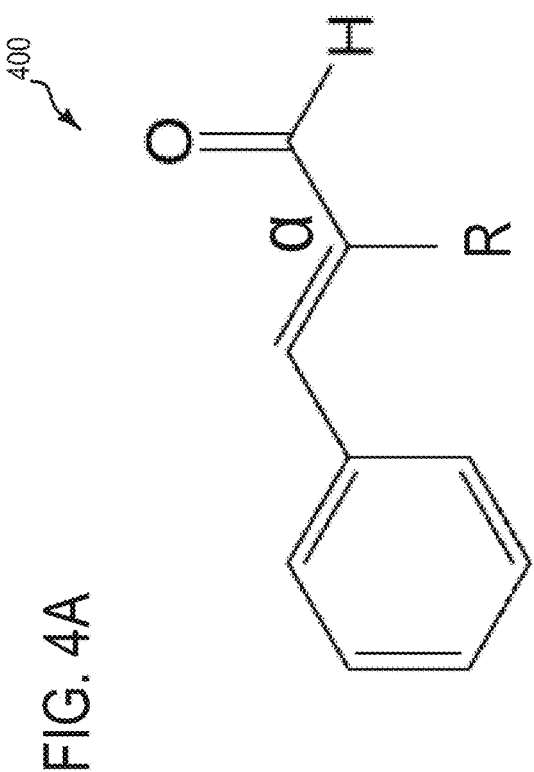
Figure 11:
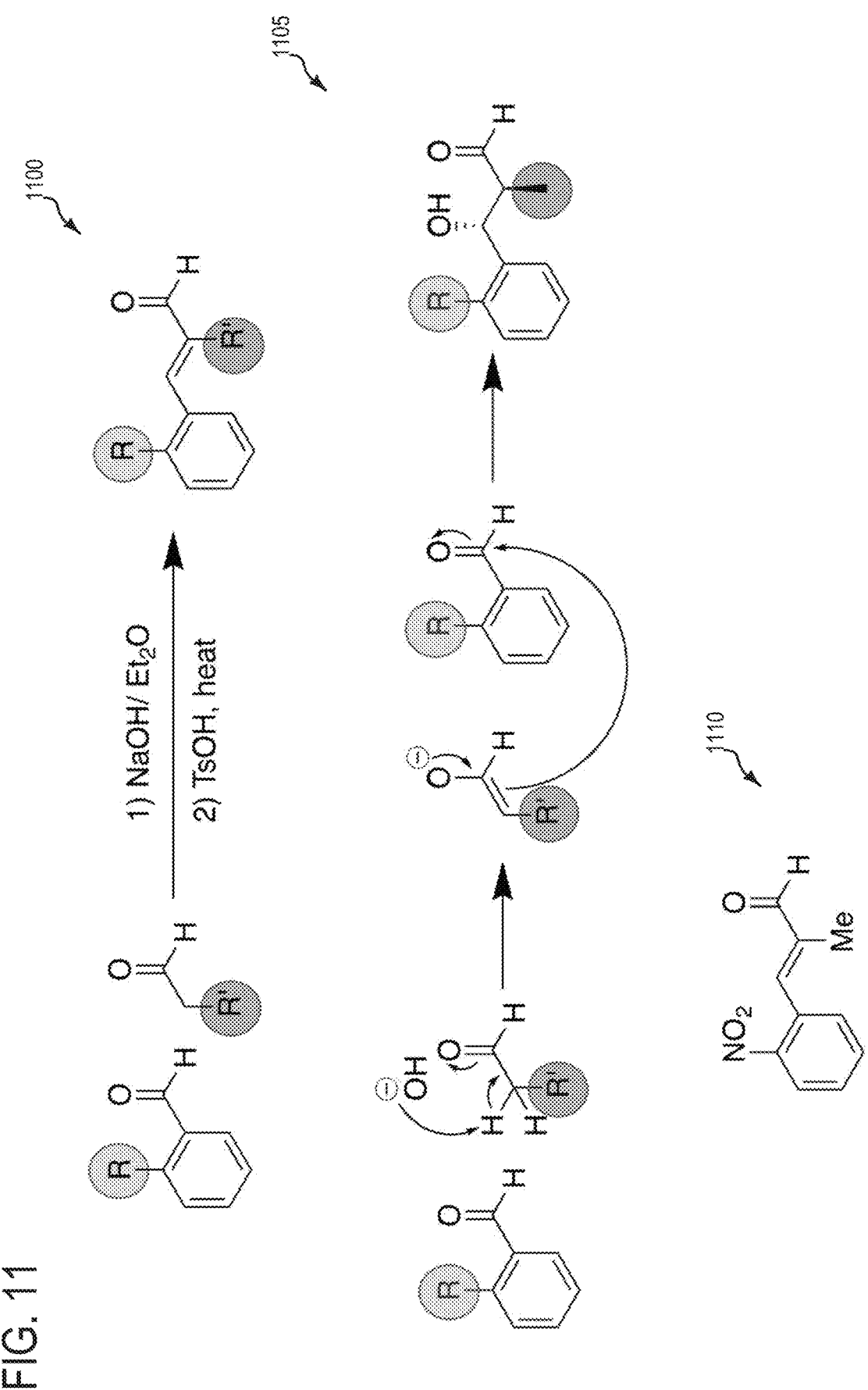
FIG. 11 depicts a synthetic scheme for 2-nitro-alpha-alkylcinnamaldehyde analogs of the present disclosure.

FIG. 4C shows example illustration 450, depicting t-CA substituted at both the alpha position and the ring position. An example of such a compound relevant to the present disclosure is depicted by compound (9) at FIG. 5A. Compound (9) is 2-nitro-α-methylcinnamaldehyde. Other examples of structural analogs of t-CA substituted at both the alpha position and the ring position are depicted by compounds (10)-(15) at FIG. 5B. Specifically, compound (10) is 2-nitro-α-ethylcinnamaldehyde, compound (11) is a 2-nitro-α-isopropylcinnamaldehyde, compound (12) is 2-nitro-α-propylcinnamaldehyde, compound (13) is 2-nitro-α-butylcinnamaldehyde, compound (14) is 2-nitro-α-amylcinnamaldehyde and compound (15) is 2-nitro-α-hexylcinnamaldehyde. An example reaction scheme for synthesis of 2-nitro-alpha-alkylcinnamaldehyde analogs of the present disclosure is depicted at FIG. 11. Specifically, at FIG. 11, reaction scheme 1100 broadly depicts how a 2-nitro-alpha-alkylcinnamaldehyde compound may be synthesized. Reaction scheme 1105 shows a more detailed mechanistic scheme. The synthesis schemes at FIG. 11 may be used, for example, to generate 2-nitro-alpha-alkylcinnamaldehyde compounds depicted by numeral 1110. While not explicitly illustrated at FIGS. 5A-5B, other examples of structural analogs of t-CA substituted at both the alpha position and the ring position may include analogs that include an electron-withdrawing group at one or more of an ortho, a meta, and a para position of t-CA, and an alkyl group at an alpha position of t-CA. Also relevant to the present disclosure but not included at FIGS. 5A-5B is hydrocinnamaldehyde and 2-methoxycinnamaldehyde.

Selection of substitution groups and/or positions to substitute t-CA may be based on increasing lipophilicity as compared to t-CA, for example. In other examples, the selection of substitution groups and/or positions to substitute t-CA may be based on making the aldehyde section of the particular analog more reactive with an oxidizing species in CYP2A6, to increase inhibitor potency. Such selection of substitution groups and/or positions may be based on a current understanding of how aldehydes are converted by CYP enzymes to metabolites that form heme adducts. In still other examples, selection of substitution groups and/or positions may be chosen to stabilize a carbon radical following deformylation, which may increase inhibitor potency. For example, adding electron-withdrawing groups (e.g. F, Cl Br, $CF_3$ or $NO_2$) at one or both of the alpha position and the ring may make the aldehyde more reactive. It may be understood that the structural analogs are not limited to those depicted at FIGS. 5A-5B, but may include any one of the structures depicted at FIGS. 5A-5B, but in a reduced form where the double bond (C=C) (between the aldehyde and the ring) is reduced to a single bond (C—C).

It may be understood that the mechanistic details of how t-CA inhibits CYP2A6 are not well-established. Thus, it may be understood that there is no theoretical framework which may readily lead one of ordinary skill in the art to know what structural analogs may lead to inhibitors that are more potent than t-CA. Moreover, because small structural changes to t-CA may result in differences in the mechanistic details of inhibition, one of ordinary skill may not readily predict which structural analogs of t-CA may increase potency. That is, structural changes may lead to changes in the reactivity of the molecule, and how it interacts with CYP2A6, and such changes are not readily predicted because the mechanism of action has not been studied extensively.

Based on the above, the following description and examples further highlight the compounds, formulations and methodologies of the present disclosure.

I. EVALUATION OF SELECTIVITY, POTENCY AND INHIBITION PARAMETERS OF HUMAN CYP2A6 BY T-CA AND STRUCTURAL ANALOGS THEREOF

Example 1. Computational Approach

An initial approach involved in silico screening using molecular modeling simulation software (e.g., Autodock and Autodock Vina) where structural analogs of t-CA were bound to a crystal structure of CYP2A6 (e.g., structure 1Z10) to estimate binding affinity ($K_D$) and binding orientation between CYP2A6 and each analog. Pymol software may be used for rendering images from the docking studies. This initial approach may prioritize compounds for wet lab experiments. t-CA analogs may thus be prioritized based on the disassociation constants ($K_D$) that the docking studies provide. $K_D$ values indicate affinity, and it may be expected to identify a structure-affinity relationship for the interaction of CA-based analogs with CYP2A6. The $K_D$ values may be compared with the $K_S$ and $IC_{50}$ values (discussed below) to determine how well the in silico method predicts affinity values from bench experiments. FIG. 6 depicts an example dataset 600, showing a partial summary of the computational docking results to predict affinity ($K_D$) of the cinnamaldehyde structural analogs to CYP2A6.

Example 2. $IC_{50}$ Measurements

Promising candidates (structural analogs of t-CA) for CYP2A6 inhibition may be studied by measuring $IC_{50}$ values, using a recombinant CYP2A6 system to measure coumarin hydroxylase activity, which is a marker for activity of CYP2A6. It may be understood that $IC_{50}$ values do not provide information on the mechanism of inhibition, but rather may be utilized to provide an early assessment of potency to prioritize compounds for more detailed analysis.

Briefly, potency of t-CA (and structural analogs thereof) was evaluated by measuring $IC_{50}$ values in recombinant human CYP2A6 Supersomes™, and human liver microsomes. Coumarin hydroxylation, a marker activity for CYP2A6 as discussed above, may be used to measure CYP2A6 activity. A 96-well plate assay and fluorescence spectroscopy may be used to quantify the product, 7-hydroxycoumarin.

Referring to Table 1A below, using the methods described above for evaluation of potency, $IC_{50}$ data is indicated for inhibition of CYP2A6 by CA and analogs. Data was fit using GraphPad Prism.

TABLE 1A $IC_{50}$ data for inhibition of CYP2A6 by cinnamic analogs. Data fit using GraphPad Prism.

| Cinnamic Analog | $IC_{50}$ (µM) |
|---|---|
| 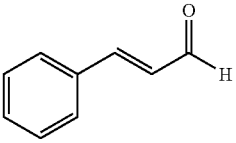 Cinnamic aldehyde | 6.9 ± 1.2 |
| 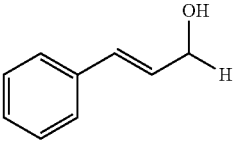 Cinnamic alcohol | 354.4 ± 4.4 |
| 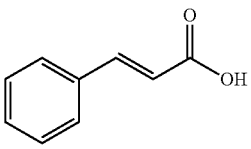 [SMILES: O=C(O)/C=C/c1ccccc1] Cinnamic acid | >2500 |

Based on Table 1A, it can be seen that t-CA is highly selective for inhibiting CYP2A6 as compared to cinnamic alcohol, and cinnamic acid.

Referring to Table 1B, further $IC_{50}$ data is indicated for select t-CA analogs of the present disclosure.

TABLE 1B $IC_{50}$ data for inhibition of CYP2A6 by structural analogs of CA of the present disclosure. Data fit using GraphPad Prism.

| Inhibitor | $IC_{50}$ (uM) | 95% CI | N |
|---|---|---|---|
| α-alkyl substituted analogs | | | |
| α-methyl-CA | 5.3 | 4.4-6.5 | 9 |
| α-amyl-CA | 65.0 | 30.5-138.5 | 9 |
| α-hexyl-CA | 64.7 | 44.4-94.3 | 9 |
| α-halogen substituted analogs | | | |
| α-chloro-CA | 3.3 | 2.8-3.8 | 9 |
| α-bromo-CA | 2.8 | 2.1-3.8 | 12 |
| Reduced, Oxime, Nitrile, and β-phenyl CA analogs | | | |
| hydro-CA | 48.3 | 40.1-58.1 | 9 |
| Cinnamaldehyde oxime | 8.0 | 7.0-9.1 | 9 |
| cinnamonitrile | 8.8 | 6.7-11.5 | 9 |
| β-phenyl CA | 147.6 | 113.9-191.3 | 9 |
| ortho-substituted analogs | | | |
| 2-nitro-CA | 15.1 | 7.1-23.1 | 12 |
| 2,6-difluoro-CA | 3.9 | 3.0-5.2 | 9 |
| meta/para-substituted analog | | | |
| 3-nitro-CA | 409.8 | 234.7-715.4 | 8 |
| 4-nitro-CA | 307.5 | 175.5-538.9 | 9 |
| 4-bromo-CA | 58.1 | 51.4-65.6 | 9 |
| 4-chloro-CA | 30.1 | 27.5-33.0 | 9 |
| 4-fluoro-CA | 30.1 | 23.8-38.1 | 9 |
| 4-dimethylamino-CA | 100.2 | 88.8-113.2 | 9 |
| 4-diethylamino-CA | 451.4 | 217.9-935.1 | 9 |
| 4-t-butyl-α-methyl-CA | 347.7 | 217.1-557.1 | 9 |

Values from the $IC_{50}$ screens indicate that small substituents (e.g., Cl, Br, and $CH_3$) at the alpha position (next to the carbonyl group) are allowed and are more potent inhibitors than structural analogs that have larger substituents (e.g., hexyl and amyl) at the alpha position. The data also indicates that replacing the carbonyl group with a cyano (C≡N) group or oxime still results in potency similar to cinnamaldehyde. In regard to substituents on the aromatic ring, the results indicate that small substituents at the ortho position are more potent inhibitors than molecules with substituents at the meta and para positions. Also, substitution with electron withdrawing groups (i.e., $NO_2$, Cl, F, Br) on the ring is more favorable for inhibition than electron donating groups (e.g., diethylamino). Finally, larger substituents on the ring, especially at the para position are expected to be less potent inhibitors of CYP2A6.

As alluded to above, $IC_{50}$ data may not predict whether a particular compound is a time-based inhibitor of CYP2A6. For example, as will be discussed in further detail below, while α-methyl-cinnamaldehyde displayed $IC_{50}$ data similar to that of α-chloro-cinnamaldehyde, α-methyl-cinnamaldehyde is found to not be a time-dependent inhibitor of CYP2A6, while α-chloro-cinnamaldehyde is found to be a substantially more potent time-dependent inhibitor of CYP2A6 than t-CA. Such a finding thus represents an unexpected technical effect that may not be readily predicted by one of ordinary skill in the art, as will be further discussed below.

Example 3. Spectral Binding Constant (KS) Measurements

Spectral binding studies were conducted using purified heterologously expressed CYP2A6 in *Escherichia coli*. Briefly, a solution of CYP2A6 may be titrated with ligand (CA or structural analog thereof) and monitored by visible absorption spectroscopy. Absorbance changes (A386-A418) may be plotted against added ligand concentrations in order to determine dissociation constants.

In more detail, the CYP2A6 enzyme may be heterologously expressed in *Escherichia coli* and purified. The expression vector, pKK2A6dH may be used to express the enzyme. The vector contains a cDNA sequence that codes for human CYP2A6 with a deletion of the N-terminal transmembrane sequence, an alteration of several residues at the modified N-terminus to increase expression, and four histidine residues added at the C-terminus to aid in purification. Truncated versions of P450 enzymes have been shown to retain similar activity as the full-length parent enzymes while allowing for far greater yields of expressed protein and have been successfully used in kinetic and biophysical studies. Expression from the vector may be induced with the addition of IPTG to bacterial cultures. δ-Aminolevulinic acid is added during expression to supplement heme biosynthesis. The enzyme may be purified following previously reported protocols. Briefly, following cell disruption, the solubilized enzyme may be purified using $Ni^{2+}$-affinity chromatography and cation-exchange (CM sepharose) chromatography, which may lead to protein of high purity and P450 content.

Using the above-described methods, spectral ligand binding data was obtained as depicted at Table 2.

TABLE 2

Spectral ligand binding data to CYP2A6 by t-CA and structural analogs of t-CA of the present disclosure.
Data fit using GraphPad Prism.

| Inhibitor | $K_s$ (uM) |
|---|---|
| t-cinnamaldehyde | 14.9 |
| o-methoxycinnamaldehyde | 1.6 |
| hydrocinnamaldehyde | 44.8 |
| α-methyl-CA | 6.8 |
| α-ethyl-CA | 3.0 |
| α-propyl-CA | 7.8 |
| α-isopropyl-CA | 3.2 |
| α-butyl-CA | 36.8 |
| α-chloro-CA | 9.6 |
| α-bromo-CA | 8.2 |
| o-nitrocinnamaldehyde | 47.5 |
| 2,6-difluoro-CA | 7.8 |
| 4-chloro-CA | 48.9 |

For illustrative purposes, Table 2 depicts a select number of structural analogs of the present disclosure. Again, α-methyl-cinnamaldehyde, for example, displays binding affinity for CYP2A6 that is on par with α-chloro-cinnamaldehyde, yet α-methyl-cinnamaldehyde is determined (see below) to not be a time-based inhibitor of CYP2A6, whereas α-chloro-cinnamaldehyde is found to be a substantially more potent time-dependent inhibitor of CYP2A6 than t-CA.

Example 4. Evaluation of Structural Analogs for Time Dependent Inhibition of CPY2A6

Figure 7A:
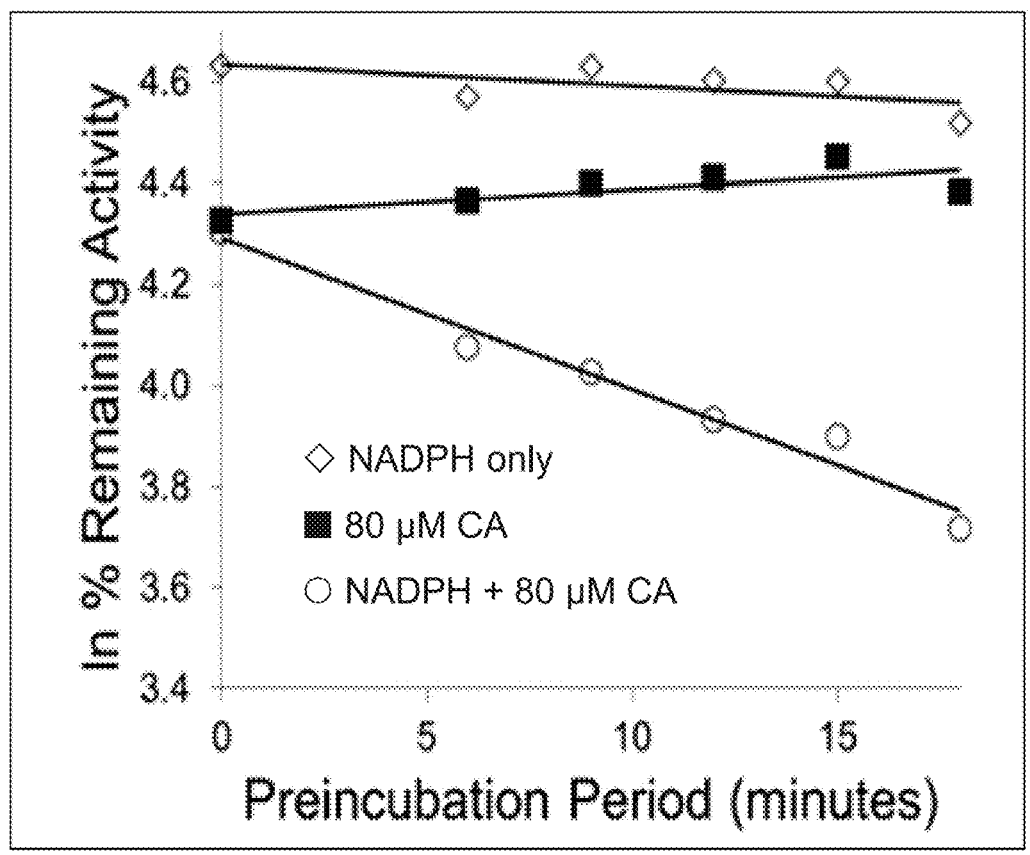
FIG. 7A illustrates that potent inhibition of CYP2A6 requires both CA and NADPH and increases with time.

Mechanism-based inhibitors are most easily identified by inhibition that increases with time. Since this type of inhibition also requires that the inhibitor is initially metabolized by the target enzyme, MBIs may be identified by evaluating the inhibition in the presence and absence of cofactors that are required for activity, such as NADPH for CYPs. Our studies indicate that t-CA inhibition (and structural analogs thereof) of CYP2A6 increases with time and is profoundly greater when t-CA (and structural analogs thereof), NADPH, and CYP2A6 are incubated together as compared to samples without NADPH. FIG. 7A depicts a representative example of the type of data illustrative of mechanism-based inhibition using t-CA as the inhibitor, where the assay is for time-dependent inhibition of 7-hydroxycoumarin formation. The data depicted at FIG. 7A was generated with recombinant CYP2A6, but it may be understood that such data may also be obtained similarly using CYP2A6 Supersomes™ and human liver microsomes.

Figure 7B:
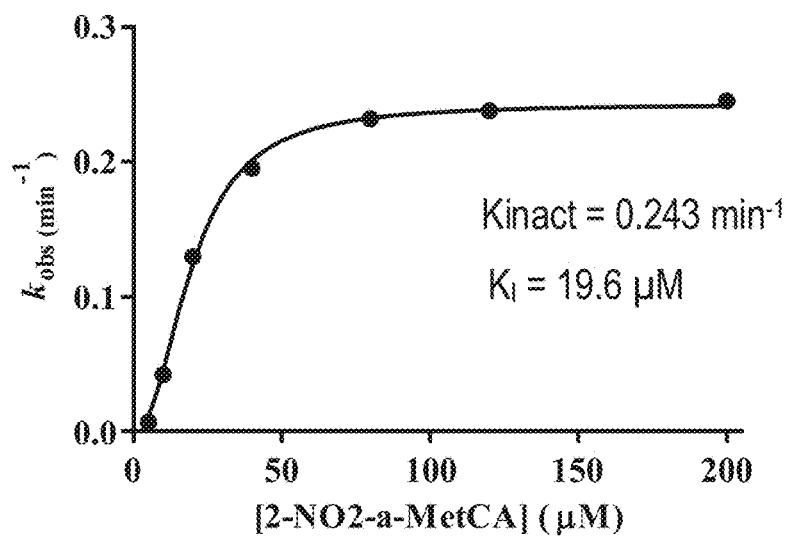
FIG. 7B depicts a representative data plot for obtaining $k_{inact}$ and $k_I$ values.

By obtaining the type of data as that depicted at FIG. 7A, plots such as that depicted at FIG. 7B (a representative example using 2-nitro-α-methylcinnamaldehyde) may be obtained and $K_{inact}$ and $K_I$ values may be obtained using nonlinear regression (e.g., via Graphpad Prism) and equation 1:

$$K_{obs} = k_{inact} * [I]/K_I + [I] \qquad (1)$$

Table 3 illustrates a summary of time-dependent inhibition parameters of CYP2A6 for t-CA and structural analogs of the present disclosure using coumarin hydroxylase activity as a readout of inhibition in a recombinant CYP2A6 system. As indicated, α-chloro-cinnamaldehyde, o-nitro-CA (2-nitro-CA), o-nitro-α-methyl-CA (2-nitro-α-methyl-CA), o-trifluoromethyl-CA (2-trifluoromethyl-CA) and 2,6-difluoromethyl-CA are all more potent inhibitors than t-CA, with α-chloro-cinnamaldehyde being over 30-fold more potent. Such a result is unexpected and cannot be readily predicted by $IC_{50}$ data and binding data as discussed above. Furthermore, the substantial increased potency observed for α-chloro-cinnamaldehyde cannot be generalized as being simply due to the presence of a halogen (e.g., electron-withdrawing group), as α-bromo-CA showed less potency as compared to t-CA, and α-fluoro-CA (refer to FIG. 8) was shown to not be a time-dependent inhibitor at all. Thus, the potency observed for α-chloro-cinnamaldehyde represents an unexpected result. For example, based on the result for α-fluoro-CA (refer to FIG. 8) that shows α-fluoro-CA is not a time-dependent inhibitor, it may be expected that α-chloro-cinnamaldehyde would also not be a time-dependent inhibitor, but that is not what is observed.

TABLE 3

Time-dependent inhibition screen of t-CA and structural analogs thereof using a recombinant CYP2A6 system

| Analog | $k_{inact}$ (min$^{-1}$) | $k_I$ (μM) | $k_{inact}/k_I$ | Fold difference (with respect to CA) |
|---|---|---|---|---|
| t-CA | 0.039 | 27.2 | 0.00143 | 1 |
| o-methoxy-CA | not measured | not measured | n/a | n/a |
| Hydro-CA | 0.116 | 85 | 0.00136 | 0.96 |
| α-bromo-CA | 0.017 | 36.3 | 0.00047 | 0.32 |

TABLE 3-continued

Time-dependent inhibition screen of t-CA and structural analogs thereof
using a recombinant CYP2A6 system

| Analog | $k_{inact}$ (min$^{-1}$) | $k_I$ (µM) | $k_{inact}/k_I$ | Fold difference (with respect to CA) |
|---|---|---|---|---|
| α-chloro-CA | 0.15 | 3.4 | 0.044 | 30.7 |
| o-nitro-CA | 0.223 | 13.9 | 0.0160 | 11.2 |
| o-nitro-α-methyl-CA | 0.243 | 19.6 | 0.0124 | 8.7 |
| m-nitro-CA | 0.083 | 89.6 | 0.00093 | 0.65 |
| p-nitro-CA | 0.039 | 92.1 | 0.00042 | 0.29 |
| o-trifluoromethyl-CA | 0.142 | 52.6 | 0.00270 | 1.9 |
| 2,6-difluoromethyl-CA | 0.244 | 47.2 | 0.00517 | 3.6 |

Figure 8:
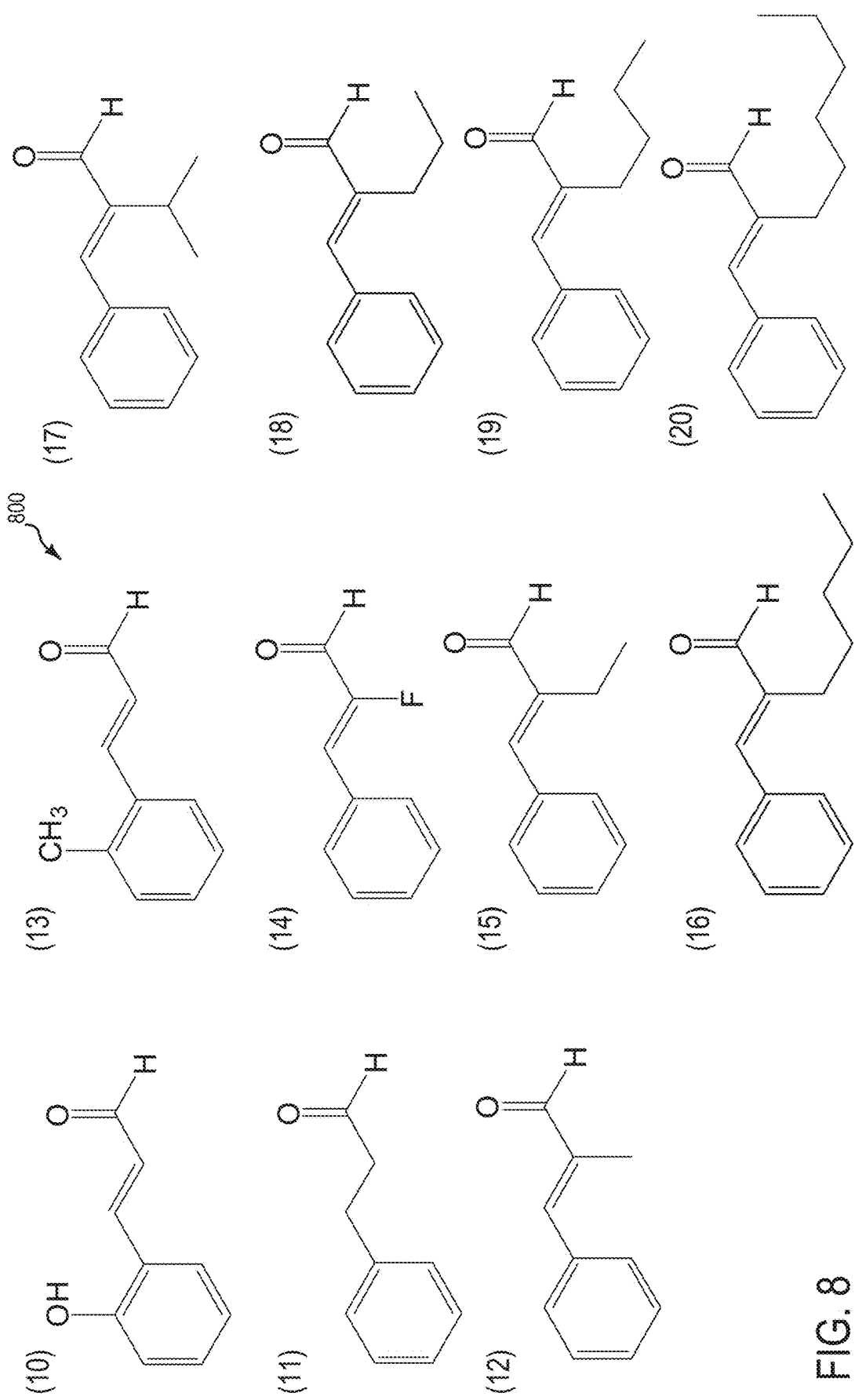
FIG. 8 depicts a number of structural analogs of t-CA of the present disclosure found to not display time-dependent inhibition of CYP2A6.

In fact, a number of structural analogs not depicted at Table 3 above were found to not be time-dependent inhibitors of CYP2A6. As mentioned above, examples of such compounds are depicted at FIG. 8. More specifically, the compounds depicted at FIG. 8 displayed similar profiles as that shown above at FIG. 7A for NADPH only (diamonds at FIG. 7A), or t-CA only (black squares at FIG. 7A), as compared to time-dependent inhibitors (circles at FIG. 7A). Compounds found not to be time-dependent inhibitors included 2-hydroxy-t-CA, hydro-CA, α-methyl-CA, 2-methyl-CA, α-fluoro-CA, α-ethyl-CA, α-pentyl-CA, α-butyl-CA, α-isopropyl-CA, α-propyl-CA α-butyl-CA, and α-hexyl-CA.

The fact that t-CA structural analogs substituted at the alpha position with alkyl groups (e.g., α-methyl-CA, 2-methyl-CA, α-ethyl-CA, α-pentyl-CA, α-butyl-CA, α-isopropyl-CA, α-propyl-CA α-butyl-CA, and α-hexyl-CA) were found to not be time-dependent inhibitors renders the finding that o-nitro-α-methyl-CA shows improved inhibition parameters (8.7-fold increase over t-CA) unexpected.

The above-discussed approach regarding evaluation of selectivity, potency and inhibition parameters of human CYP2A6 by t-CA and structural analogs thereof may be similarly applied to evaluation of the same parameters with regard to CYP2A13. As one representative example, inhibition of CYP2A13 as monitored via coumarin hydroxylase activity as a readout of inhibition in a recombinant CYP2A13 system shows that 2-nitro-cinnamaldehyde has a $K_I$ of 30.95 µM, and a $K_{inact}$ of 0.12161 min$^{-1}$, resulting in a $K_{inact}/K_I$ of 0.00407.

II. EVALUATION OF 'DRUGGABILITY' OF CA AND STRUCTURAL ANALOGS THEREOF AS TOBACCO CESSATION AGENTS

There are many reasons why a potent in vitro inhibitor may not become an effective drug, including instability, toxicity, and drug-drug interactions. Thus, t-CA and structural analogs thereof may be evaluated as to promising drug-like characteristics, discussed in the examples below.

Example 5. Evaluation of the Potential of the Interaction between t-CA (And Structural Analogs Thereof) and CYP2A6-Mediated Nicotine Metabolism To evaluate the potential of the interaction between t-CA (and structural analogs thereof) and CYP2A6-mediated nicotine metabolism, a model may be used that incorporates mechanism-based inhibition parameters (i.e., $K_I$ and $k_{inact}$), an intrinsic degradation rate of CYP2A6 in the absence of inhibitors ($k_{deg}$), and a fraction of a nicotine dose metabolized by CYP2A6 ($f_m$), to predict changes in the nicotine area under the curve (AUC), a parameter indicative of a patient's exposure to a drug over time. Equation 2 shows how the AUC changes in the presence of an inhibitor. In the context of this example, AUCi/AUC refers to the AUC for nicotine in the presence of CA divided by the AUC in the absence of t-CA.

Prediction of $AUC$ changes in the presence of a mechanism-based inhibitor.     Equation 2

$$\frac{AUC_i}{AUC} = \frac{1}{\left(\frac{f_{m,CYP}}{1 + \left(\frac{k_{inact} \cdot [I]}{k_{deg} \cdot (K_I + [I])}\right)}\right) + (1 - f_{m,CYP})}$$

Using data from our initial studies, Equation 2 predicts profound changes in nicotine AUC, even at low plasma concentrations of t-CA (depicted as a representative example at Table 4). That is, a 4.5-fold change in nicotine AUC is predicted at just 1 µM t-CA.

TABLE 4

Predicted changes in AUC for oral nicotine in the presence of varying concentrations of CA.

| [CA] µM | $f_m^d$ | $k_{deg}^e$ (per min) | AUC Fold Increase Supersomes | AUC Fold Increase Microsomes |
|---|---|---|---|---|
| 0.1 | .86 | .00044 | 1.4 | 1.8 |
| 1 | .86 | .00044 | 3.4 | 4.5 |
| 10 | .86 | .00044 | 6.0 | 6.4 |

CA = cinnamic aldehyde;
$^d f_m$ = fraction of a nicotine dose metabolized by CYP2A6;
$^e k_{deg}$ = degradation rate of CYP2A6 in vivo.

In humans, t-CA is completely absorbed upon oral administration. This has also observed in rats, for which full pharmacokinetic studies are available. Converting the dose in rats to humanized equivalent doses can estimate the doses necessary to achieve low µM concentrations of CA in humans. The Food and Drug Administration suggests using the body surface area (BSA) normalization method to extrapolate animal doses to human doses. In rats a single 250 mg/kg oral dose generated a t-CA blood concentration of 7.6 µM. With the BSA method, t-CA doses of 32 mg and 320 mg per day are estimated to achieve concentrations of 0.1 and 1 µM in humans. Notably, the estimated range of t-CA exposure when cinnamon powder is used for diabetes is 8 to 275 mg/day.

Since smokers titrate nicotine plasma concentrations to a defined range, and poor metabolizers smoke fewer cigarettes than rapid metabolizers, the data presented in Example 5 suggests that t-CA can profoundly impact nicotine clearance, carcinogen exposure, and potentially impact dosing of nicotine replacement therapy. Substantial and prolonged inactivation may occur during first-pass liver exposure in which the concentration of t-CA may be higher than the concentration in the systemic circulation. Therefore, a dose that results in 1 µM t-CA (or structural analogs thereof) in the blood, may result in even greater reduction in nicotine metabolism than predicted by the model, especially for individuals who are rapid metabolizers of nicotine. Overall the modeling and pharmacogenetic data support the hypothesis that t-CA (and structural analogs thereof) may impact smoking cessation rates.

Turning to Table 5, it depicts exemplary $K_I$, $k_{inact}$, and AUC predictions for several structural analogs of the present disclosure, as compared to t-CA.

TABLE 5

$k_I$, $k_{inact}$ and AUC predictions

| Analog | $k_{inact}$ (min$^{-1}$) | $k_I$ (uM) | $k_{inact}/k_I$ | AUC fold increase |
|---|---|---|---|---|
| t-CA | 0.056 | 27.2 | 0.002059 | 1.71-2.69 |
| α-chloro-CA | .15 | 3.4 | 0.043989 | 2.44-4.22 |
| α-bromo-CA | .017 | 36.3 | 0.000463 | 1.35-1.84 |
| hydro-CA | .116 | 85.0 | 0.001365 | 1.71-2.67 |

To empirically determine inhibition of nicotine metabolism, an HPLC-MS/MS method may comprise use of a Phenomenex Kinetix C18 column (2.1×50 mm; 2.6 micron) and a mobile phase consisting of 0.2% ammonia in water (solvent A) and acetonitrile (solvent B). To separate nicotine, cotinine, and the internal standard (D3-cotinine) the mobile phase may be ramped from 5%-95% B over 5 minutes, followed by a column wash by holding 95% B for 1 minute and re-equilibrating to 5% B for 3 minutes. Cotinine and Nicotine may be quantified by multiple reaction monitoring (MRM) using the 177.4/80.2 Da (parent/transition) fragment for cotinine, the 163.1/117.2 fragment for nicotine and the 180.06/100.9 fragment for D3-cotinine. To determine time dependent inhibition parameters human liver microsomes (200-donor pool; 5 mg/ml) may be preincubated in a total volume of 140 µl for 5 minutes at 37° C. in buffer (50 mM potassium phosphate, pH=7.4). Aliquots (20-µl) may be removed from the primary incubation at multiple time points and diluted to 200 µl in incubation buffer containing cytosol (1 mg/ml protein), nicotine (50 µM) and NADPH (1 mM), and incubated for an additional 15 minutes at 37° C. Incubations may be terminated with 200 µl acetonitrile and 100 µl of 5 µg/mL D3-cotinine (internal standard) may be added. The samples may be analyzed by the HPLC-MS/MS method described above. The inhibitors identified to be potent inhibitors of CYP2A6 may be assessed in human hepatocytes, a more physiologically relevant system.

Example 6. Evaluation of Metabolic Stability and Drug-Likeness of T-CA and Structural Analogs Thereof To evaluate metabolic stability and drug-likeness of t-CA and structural analogs thereof, experiments may be conducted in human liver microsomes with cytosol. t-CA and structural analogs thereof may be incubated in microsomes (0.5-0.75 mg/mL) and cytosol with phosphate buffer (pH=7.4) and NADPH for 60 minutes, where aliquots may be analyzed by HPLC at specific time points. Standard curves may be used to quantify loss of each of t-CA and structural analogs thereof, as a function of time. Specifically, an HPLC-fluorescence assay for CA may be used to ascertain stability, and which may similarly be used to monitor stability of structural analogs.

Lipinkski's rule of five (RO5) was used to evaluate the drug-likeness of CA and structural analogs thereof. Each analog may be given a score between 0 (not drug-like) and 4 (drug-like) based on how well it fits the criteria of the RO5, the RO5 comprising 1) molecular weight less than 500 Da, log P<5 (measure of lipophilicity), number of hydrogen bond donors (HBD)<5, and the number of hydrogen bond acceptors (HBA)<10. Molecular weight and log P values may be obtained from PubChem and ChemSpider. A representative sample is depicted at Table 6.

TABLE 6

Drug-likeness of CA and CA analogs

| Structure | MW | Log P | HBD | HBA | Score |
|---|---|---|---|---|---|
| (cinnamaldehyde) | 132.16 | 1.9 | 0 | 1 | 4 |
| (α-bromo cinnamaldehyde) | 211.06 | 2.7 | 0 | 1 | 4 |
| (2,6-difluoro cinnamaldehyde) | 168.14 | 2.3 | 0 | 1 | 4 |

III. DEVELOPMENT AND EVALUATION OF FORMULATIONS OF T-CA (AND STRUCTURAL ANALOGS THEREOF) FOR BIOAVAILABILITY AND INHIBITION OF NICOTINE METABOLISM

Figure 9A:
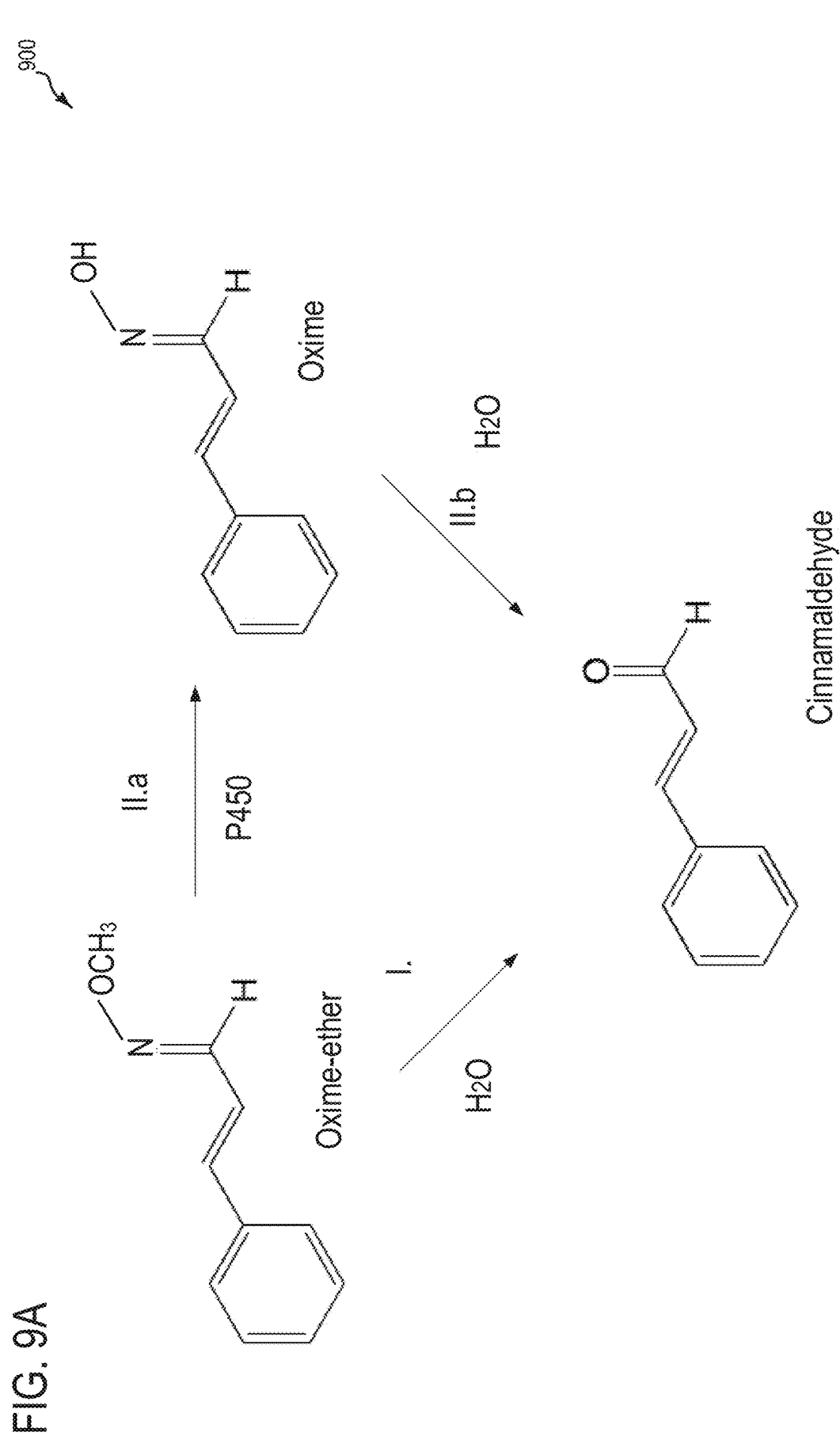
FIG. 9A depicts an example reaction scheme of routes whereby an oxime-ether is metabolized to t-CA (or structural analogs thereof)
Figure 9B:
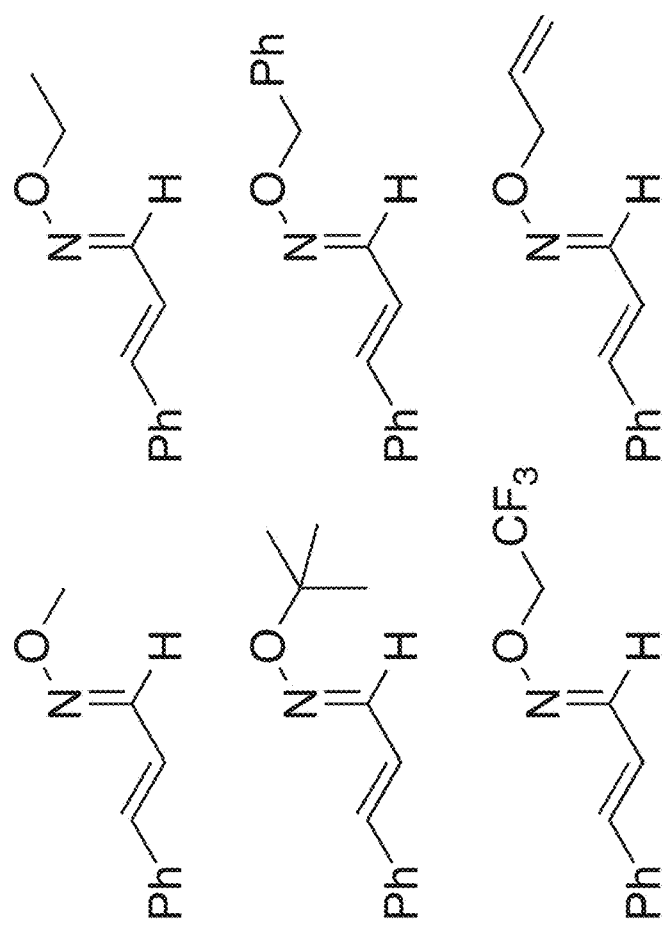
FIG. 9B depicts examples of oxime ethers of the present disclosure, which may be used for structural analogs of t-CA.

As discussed above, previous results indicate that t-CA (and structural analogs thereof) is a MBI of CYP2A6, predicting substantial changes in nicotine clearance. A potential barrier for t-CA (and structural analogs thereof) to serve as a tobacco cessation agent may be rapid degradation or poor adsorption in the gastrointestinal tract or the liver. Studies in rats have shown that t-CA is metabolized rather quickly, suggesting that dosages may need to be relatively high to achieve sufficient CYP2A6 inhibition in vivo. A principal of toxicology is the relationship between dose and toxicity, with high-dosed drugs typically associated with a greater risk for toxicity. To overcome such issues, formulations and prodrug forms (oxime-ethers) of t-CA (and structural analogs thereof) are discussed herein. Both may improve absorption, distribution, metabolism, and excretion (ADME) properties and allow for lower dosing while maintaining effectiveness. Thus, an aspect of the present disclosure is evaluation of formulations of t-CA (and structural analogs thereof) for loading, stability, and t-CA (and structural analogs thereof) release characteristics (see III.i), synthesis of oxime-ether prodrug forms of t-CA (and structural analogs thereof) as well as evaluation of their metabolic stability (see III.ii), measurement of intestinal absorption and CYP2A6 inhibition potency (see III.iii), and use of a rat model to determine systemic exposure of CA and to measure the PK parameters of the oxime-ether prodrug (see III.iv). Turning to FIG. 9A, an example scheme 900 depicts how t-CA (or structural analogs thereof) may be released from an oxime-ether by one of two routes (route I or route II which includes steps II.a and II.b). The oxime-ether may be hydrolyzed in the presence of water (route I), or may first undergo O-dealkylation by cytochrome P450 enzymes in the liver (route II.a), followed by hydrolysis (route II.b). Turning to FIG. 9B, example illustration 950 depicts oxime ethers of the present disclosure. The oxime ethers depicted at FIG. 9B are shown with regard to t-CA, but it may be understood that t-CA as depicted at FIG. 9B may be replaced with any of the structural analogs depicted at FIGS. 5A-5B.

III.i Evaluation of Formulations of CA for Loading, Stability and CA (and Structural Analogs Thereof) Release Two formulations of CA (and structural analogs thereof) may be prepared, a self-emulsifying drug delivery system (SEDDS), and a co-solvent solution using Pluronic® polymers or polaxamers which are tri-block copolymers of poly(ethylene oxide)-poly(propylene oxide)-poly(ethylene oxide) (PEO-PPO-PEO). The SEDDS system may be developed by determining the best surfactant/mixture of surfactants that will match the Hydrophile-Lipophile Balance (HLB) value for the t-CA (or structural analogs thereof) oil. The system may be assessed for t-CA (or structural analogs thereof) loading and stability at room temperature by monitoring size and zeta potential. t-CA (and structural analogs thereof) release may be assessed by a dialysis method under sink conditions. The SEDDS may deliver nanoscale delivery of t-CA (and structural analogs thereof) at high concentrations to allow for greater absorption similar to the marketed SEDDS formulation, Neoral®.

The co-solvent system may be prepared by determining the best polaxamers to enhance the oral bioavailability of the CA. Polaxamers are tri-block co-polymers and biologic response modifiers that have shown the ability to increase the bioavailability and alter the PK of molecules co-delivered with them. Thus CA incorporated into polaxamers may be prepared by solvation method. One potential issue includes challenges associated with solubilizing high concentrations of CA (and structural analogs thereof) in the co-solvent system using the polaxamers. To address this, other block co-polymers like PEG-PCL or PEG-PLA, which have different polarities, may be utilized to achieve higher drug concentrations.

Figure 10:
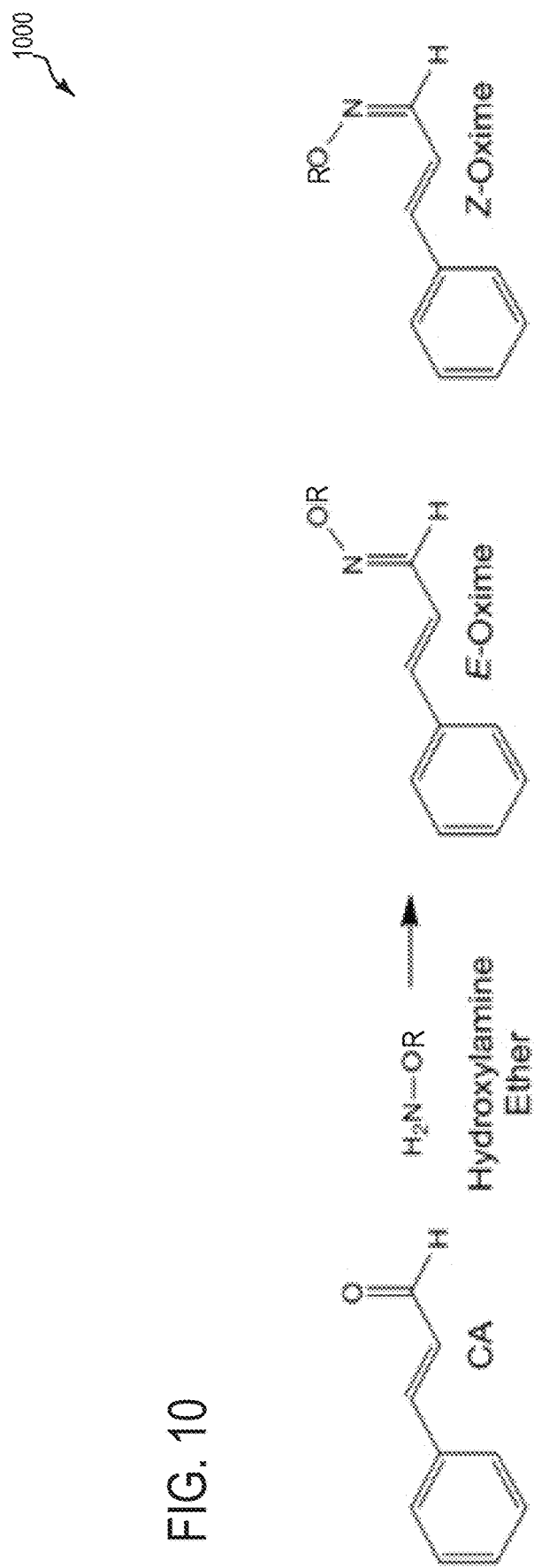
FIG. 10 depicts a general synthetic scheme for oxime ethers of t-CA and structural analogs of t-CA.

III.ii Synthesis of Prodrug Forms of CA Based on an Oxime-Ether Chemical Scaffold and Evaluation of Metabolic Stability Synthesis of oxime compounds was conducted via condensation of t-CA (and structural analogs thereof) with a variety of hydroxylamine ethers ($H_2N$—OR), where R is one of methyl, ethyl, etc. The hydroxylamine derivatives are available from commercial sources and FIG. 10 broadly depicts reaction scheme 1000 for synthesizing the oxime compounds which may include heating t-CA and $H_2N$—OR together in a protic solvent. Reaction conditions may be optimized to suit the reactivity of particular combinations. A weak acid catalyst at sub-stoichiometric quantities may be utilized to accelerate the reaction. Metabolic stability and generation of t-CA (and structural analogs thereof) may be assessed using human liver microsomes with cytosol. The oxime-ethers may be incubated in microsomes and cytosol with phosphate buffer. Aliquots may be analyzed by LC-MS/MS at specific time points to evaluate a degradation rate of the prodrug as a function of time. Standard curves of t-CA (and structural analogs thereof) may be generated to quantify a rate of generation of t-CA (and structural analogs thereof).

III.iii Assessment of Intestinal Absorption of the Above-Mentioned Formulations and the Prodrug Form of CA (and Structural Analogs Thereof) Assessed Using CACO-2 Cells, and CYP2A6 Inhibition Potency Assessed in Human Hepatocytes Delivery systems (the above-mentioned formulations) may be assessed in vitro in Caco-2 models to determine efflux across the monolayer. Caco-2 cells may be grown to confluence over 20 days in 24 well transwell plates, and t-CA alone (or structural analogs thereof), in formulations, or as the oxime prodrug may be added to the apical insert at various concentrations. The wells may be incubated at 37° C. with shaking. At 0, 60, and 120 min 20 µL samples may be withdrawn from the apical side, and 200 µL samples may be taken from the basolateral side at 0, 15, 30, 45, 60, 90, and 120 min. t-CA (and structural analogs thereof) concentrations may be assessed by LC-MS/MS, and the apparent partition coefficient ($P_{app}$) may be calculated. Inhibition of nicotine metabolism may be evaluated in human liver microsomes with cytosol, followed by studies in human hepatocytes (a more physiologically relevant system). Oxime flux may additionally be determined across the Caco-2 monolayer for comparison to t-CA (and structural analogs thereof).

III.iv Measurement of In Vivo PK Parameters of an Oxime-Ether Prodrug to Determine a Resulting Systemic Exposure of t-CA from the Formulations/Prodrug Adult male Sprague-Dawley rats (300-400 g) may be cannulated. Animals may be divided into 3 groups of 12 animals: one for each optimized t-CA (and structural analogs thereof) formulation, and oxime prodrug (to generate t-CA or structural analogs thereof). Animals may be dosed orally via gavage with t-CA (or structural analogs thereof) in the formulations at 250 mg/kg; a dose below the reported $LD_{50}$. At 5, 15, 30, 60, 120, 180, 360, 720, and 1440 minutes post-administration 0.1-0.2 mL of blood may be collected. t-CA (and structural analogs thereof) concentrations may be assessed using LC-MS/MS, and PK parameters may be determined using WinNonlin. PK data may be incorporated into PBPK models.

Higher AUC values for the t-CA (and structural analogs thereof) in formulations and oxime-ether prodrug may be expected. The formulations may deliver higher doses of CA (and structural analogs thereof) in both the SEDDS and the co-solvent system, as in both systems, the presence of amphipathic molecules may enhance the absorption of various molecules orally.

In this way, individuals with a dependence on nicotine may be treated to reduce said dependence. Reducing said dependence may in turn reduce a potential for adverse health implications (e.g., lower a risk of cancer, where the cancer is one or more of lung cancer, prostate cancer, bladder cancer, pancreatic cancer, head and neck cancers, esophageal cancer, kidney cancer, stomach cancer, colon cancer, acute myelogenous leukemia (AML), ovarian cancer, breast cancer, liver cancer, cervical cancer, and skin cancer) stemming from the use of nicotine-containing products. Thus, in some examples the compounds, compositions and methods of use discussed herein may relate to reducing a risk of cancer in a subject with a nicotine dependence.

In another embodiment, a pharmaceutical composition of the present disclosure may comprise one or more structural analog(s) (refer to FIGS. 5A-5B) of the present disclosure, where the structural analog is a mechanism-based inhibitor of CYP2A6. In one example, the composition may further comprise one or more of an oil and a surfactant (or one or more different oils and one or more different surfactants). In some examples, the composition may be capable of self-emulsifying in a gastro-intestinal environment, or other aqueous environment. In some examples, the composition may comprise less than 10%, less than 5%, or less than 1% by weight water. In some examples, the composition may include one or more co-solvents. The one or more co-solvents may comprise polyethylene glycol 300, polyethylene glycol 400, and propylene glycol, for example. In some examples, the oil may comprise a single long chain triglyceride, a single medium chain triglyceride, a medium chain monoglyceride, and a medium chain diglyceride. In some examples, the oil may be a blend of a monoglyceride or a diglyceride blended with either a long chain triglyceride or a medium chain triglyceride. In some examples the oil may be castor oil. In some examples, the surfactant may be polysorbate 80. In some examples, the structural analog(s) may be encapsulated in an encapsulating nanosphere. In some examples, the encapsulating nanosphere may be formed from one or more tri-block copolymers. In some examples, the one or more structural analog(s) may be incorporated into the encapsulating nanosphere via a solvation method. In some examples, the tri-block copolymers may be selected in order to enhance an oral bioavailability of the one or more structural analog(s). In some examples, the tri-block copolymers may comprise PEG PCL and/or PEG PLA.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for treating an individual with an addiction to nicotine, comprising administering to the individual a compound of one of the following chemical structure:

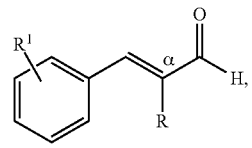

wherein the compound is one of 2-nitro-α-methylcinnamaldehyde, 2-nitro-α-ethylcinnamaldehyde, 2-nitro-α-isopropylcinnamaldehyde, 2-nitro-α-propylcinnamaldehyde, 2-nitro-α-butylcinnamaldehyde, 2-nitro-α-amylcinnamaldehyde and 2-nitro-α-hexylcinnamaldehyde, and wherein a rate at which nicotine is metabolized is reduced upon administration of the compound to the individual.

2. The method of claim 1, wherein the compound is administered orally to the individual.

3. The method of claim 1, further comprising selecting the compound based on whether the individual is an ultrafast, fast, intermediate, or slow metabolizer of nicotine.

* * * * *